United States Patent
Pande et al.

(10) Patent No.: US 12,042,257 B2
(45) Date of Patent: *Jul. 23, 2024

(54) HEART RATE ESTIMATION APPARATUS WITH STATE SEQUENCE OPTIMIZATION

(71) Applicant: TEXAS INSTRUMENTS INCORPORATED, Dallas, TX (US)

(72) Inventors: Tarkesh Pande, Richardson, TX (US); David Patrick Magee, Allen, TX (US); Rajan Narasimha, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/412,580

(22) Filed: Aug. 26, 2021

(65) Prior Publication Data

US 2021/0378535 A1    Dec. 9, 2021

Related U.S. Application Data

(60) Division of application No. 16/442,845, filed on Jun. 17, 2019, now Pat. No. 11,129,538, which is a
(Continued)

(51) Int. Cl.
*A61B 5/02* (2006.01)
*A61B 5/00* (2006.01)
*A61B 5/024* (2006.01)

(52) U.S. Cl.
CPC ...... *A61B 5/02427* (2013.01); *A61B 5/02416* (2013.01); *A61B 5/7225* (2013.01); *A61B 5/7278* (2013.01); *A61B 5/7275* (2013.01)

(58) Field of Classification Search
CPC ............ A61B 5/02416; A61B 5/02427; A61B 5/7225; A61B 5/7275; A61B 5/7278
See application file for complete search history.

(56) References Cited

U.S. PATENT DOCUMENTS

| 3,972,320 A | 8/1976 | Kalman |
| 4,312,358 A | 1/1982 | Barney |

(Continued)

FOREIGN PATENT DOCUMENTS

| CN | 1531407 A | 9/2004 |
| CN | 102697492 A | 10/2012 |

(Continued)

OTHER PUBLICATIONS

Epifanio da Franca, et al; "Analog-to-Digital Conversion" Wiley Encyclopedia of Electrical and Electronics Engineering, edited by John G. Webster, published 2000 by John Wiley & Sons, Inc. 40 pages.

(Continued)

*Primary Examiner* — Eric D. Bertram
(74) *Attorney, Agent, or Firm* — Frank D. Cimino

(57) ABSTRACT

Disclosed examples include heart rate monitor systems and methods to estimate a patient heart rate or rate of another pulsed signal, in which rate hypotheses or states, are identified for a current time window according to digital sample values of the pulsed signal for a current sample time window, and a rate change value is computed for potential rate transitions between states of the current and previous time windows. Transition pair branch metric values are computed as a function of the rate change value and a frequency domain amplitude of the corresponding rate hypothesis for the current time window, and the pulsed signal rate estimate is determined according to a maximum path metric computed according to the branch metric value and a corresponding path metric value for the previous time window.

23 Claims, 9 Drawing Sheets

Related U.S. Application Data continuation of application No. 15/237,941, filed on Aug. 16, 2016, now Pat. No. 10,321,831.

(60) Provisional application No. 62/260,029, filed on Nov. 25, 2015.

(56) References Cited

U.S. PATENT DOCUMENTS

| | | | |
|---|---|---|---|
| 5,316,008 A | 5/1994 | Suga et al. | |
| 5,730,142 A | 3/1998 | Sun et al. | |
| 5,865,755 A | 2/1999 | Golub | |
| 6,599,251 B2 | 7/2003 | Chen et al. | |
| 6,723,054 B1 | 4/2004 | Baruch et al. | |
| 7,993,275 B2 | 8/2011 | Banet et al. | |
| 8,290,575 B2 | 10/2012 | Tarassenko et al. | |
| 10,321,831 B2 * | 6/2019 | Pande | A61B 5/02416 |
| 10,729,381 B2 | 8/2020 | Pande et al. | |
| 10,758,185 B2 | 9/2020 | Pande et al. | |
| 11,129,538 B2 * | 9/2021 | Pande | A61B 5/7278 |
| 2004/0039273 A1 * | 2/2004 | Terry | A61B 5/7257 600/322 |
| 2008/0097633 A1 | 4/2008 | Jochelson et al. | |
| 2010/0280402 A1 | 11/2010 | Dunbar et al. | |
| 2011/0293195 A1 | 12/2011 | Nakagami et al. | |
| 2012/0143071 A1 * | 6/2012 | Hete | A61B 5/7257 600/504 |
| 2014/0073960 A1 | 3/2014 | Rodriguez-Llorente et al. | |
| 2014/0114147 A1 | 4/2014 | Romesburg | |
| 2014/0213863 A1 | 7/2014 | Loseu et al. | |
| 2014/0257049 A1 | 9/2014 | Soundarapandian et al. | |
| 2014/0364750 A1 * | 12/2014 | Brumfield | A61B 5/02455 600/500 |
| 2015/0094552 A1 | 4/2015 | Golda et al. | |
| 2015/0094592 A1 | 4/2015 | Ravindran et al. | |
| 2015/0112208 A1 | 4/2015 | He et al. | |
| 2015/0196256 A1 | 7/2015 | Venkatraman et al. | |
| 2015/0196257 A1 | 7/2015 | Yousefi et al. | |
| 2015/0313549 A1 | 11/2015 | Lee et al. | |
| 2015/0366469 A1 | 12/2015 | Harris et al. | |
| 2016/0089086 A1 * | 3/2016 | Lin | A61B 5/02416 600/479 |
| 2016/0317097 A1 | 11/2016 | Adams et al. | |
| 2016/0324477 A1 * | 11/2016 | Gunturi | A61B 5/721 |
| 2017/0020398 A1 * | 1/2017 | Emadzadeh | A61B 5/02438 |
| 2017/0143274 A1 | 5/2017 | Pande et al. | |
| 2017/0367657 A1 | 12/2017 | Pande et al. | |

FOREIGN PATENT DOCUMENTS

| | | |
|---|---|---|
| CN | 102843966 A | 12/2012 |
| CN | 103020472 A | 4/2013 |
| CN | 104462858 A | 3/2015 |
| CN | 105380630 A | 3/2016 |
| JP | 2001340309 A | 12/2001 |
| JP | 2011519653 A | 7/2011 |
| WO | 2005020798 A2 | 3/2005 |

OTHER PUBLICATIONS

Allen, et al; "Photoplethysmography and its application in clinical physiological measurement"; Physiological Measurement, vol. 28, No. 3; 2007; 22 pages.

Hertzman, "The Blood Supply of Various Skin Areas as Estimated by the Photoelectric Plethysmograph", Amer. J. Physiol., 1938; 1924: pp. 328-400.

Wijshoff et al., "Reducing Motion Artifacts in Photoplethysmograms by Using Relative Sensor Motion: Phantom Study", J. Biomed. Opt. 17(11), 117007 (Nov. 29, 2012), 16 pgs.

Fukushima et al., "Estimating Heart Rate Using Wrist Type Photoplethysmography and Acceleration Sensor While Running", Engineering in Medicine and Biology Society (EMBS), 2012 Annual Int'l Conf. of the IEEE 2012, pp. 2901-2904.

Zhang, et al., "Troika: A General Framework for Heart Rate Monitoring Using Wrist-Type Photoplethysmographic Signals During Intensive Physical Exercise", IEEE Trans Biomedical Engineering, vol. 62, No. 2, Feb. 2015, 10 pgs.

Schack, et al., "A New Method for Heart Rate Monitoring During Physical Exercise Using Photoplethysmopraphic Signals", European Signal Processing Conf., Sep. 2015 (EUSIPCO 2015), 5 pgs.

Karantonis et al., "Implementation of a Real-Time Human Movement Classifier Using a Triaxial Accelerometer for Ambulatory Monitoring", IEEE Transactions on Information Technology in Biomedicine, vol. 10, No. 1, Jan. 2006, pp. 156-167.

International Search Report for PCT/US2016/063780 dated Mar. 6, 2017 (2 pages).

Office Action for Chinese Patent Application No. 201611067402.9, with Search Report, dated Jul. 22, 2020, 6 pages.

CN102843966A, Machine Translation, 21 pages.
CN1531407A, Machine Translation, 23 pages.
JP2011519653A, Machine Translation, 16 pages.
CN102697492A, Machine Translation, 22 pages.
CN104462858A, Machine Translation, 12 pages.
CN103020472A, Machine Translation, 28 pages.
CN105380630A, Machine Translation, 31 pages.

Amann, et al., "Detecting Ventricular Fibrillation by Time-Delay Methods," IEEE Transactions on Biomedical Engineering, vol. 54, No. 1, 1, Jan. 2007, pp. 174-177.

Shao, Zhi-Gang, "Network Analysis of Human Heartbeat Dynamics," Applied Physics Letters 96, 073703 (2010), 3 pages.

* cited by examiner

HEART RATE ESTIMATION APPARATUS WITH STATE SEQUENCE OPTIMIZATION

CROSS-REFERENCE TO RELATED APPLICATIONS

This application is a divisional of U.S. patent application Ser. No. 16/442,845 filed Jun. 17, 2019, now U.S. Pat. No. 11,129,538, which is a continuation of U.S. patent application Ser. No. 15/237,941 filed Aug. 16, 2016, now U.S. Pat. No. 10,321,831, which claims priority to U.S. Provisional Patent Application Ser. No. 62/260,029 filed Nov. 25, 2015, the entireties of each of which are incorporated herein by reference.

BACKGROUND

A photoplethysmogram ("PPG") is an optically obtained volumetric measurement of an organ (an optical plethysmogram). Photoplethysmography can be used in wearable activity monitors, medical equipment or other systems to optically detect blood volume changes in blood vessels to monitor blood flow, blood content, respiration rate and other circulatory conditions, where the intensity of back scattered light correlates to the amount of blood volume. PPG signals can be obtained in a number of different ways, including assessing absorption of light transmitted through, or reflected from, a patient's skin. A light source at a particular wavelength (typically, red, infrared or green) directs light toward the patient's skin. A photodiode or other optical sensor generates the PPG signal indicating the measured light transmission or reflection, and changes in the PPG signal can be used to detect the pulse rate of the patient's heart. PPG based heart rate estimation during motion is difficult, as motion artifacts show up in the PPG signal. The motion artifacts are caused by hemodynamic effects, tissue deformation, and sensor movement relative to the skin. Motion compensation techniques have been proposed to remove the motion component in the PPG signal using information from an external sensor reference, such as an accelerometer. Some approaches use spectrum subtraction to first remove the spectrum of the acceleration data from that of the PPG signal prior to heart rate estimation. Another motion compensation approach uses compressed sensing techniques combined with signal decomposition for de-noising and spectral tracking. The PPG signal fidelity can be further improved using normalized least mean squares (NLMS) and non-coherent combination in the frequency domain. A patient heart rate can be estimated from PPG signals using time-domain analysis, for example, band-pass filtering with a zero crossing detection, but this approach is largely unsuitable in the presence of motion artifacts. Frequency domain analysis generally involves choosing a highest peak in a frequency spectrum as the estimated patient heart rate. However, the PPG frequency spectrum typically includes multiple peaks within a range of realistic patient heart rates, and the dominant frequency domain peak does not always correspond to the actual patient heart rate, particularly in the presence of motion artifacts.

SUMMARY

Disclosed examples include heart rate monitor systems and methods to estimate a patient's heart rate or a rate of another pulsed signal using state sequence tracking. Heart rate hypotheses, or states, are identified for a current time window according to digital sample values of the pulsed signal for a current sample time window, and a rate change value is computed for potential rate transitions between states of the current and previous time windows. Transition pair branch metric values are computed as a function of the rate change value and a frequency domain amplitude of the corresponding rate hypothesis for the current time window, and the pulsed signal rate estimate is determined according to a maximum path metric computed according to the branch metric value and a corresponding path metric value for the previous time window.

DETAILED DESCRIPTION OF EXAMPLE EMBODIMENTS

Figure 1:
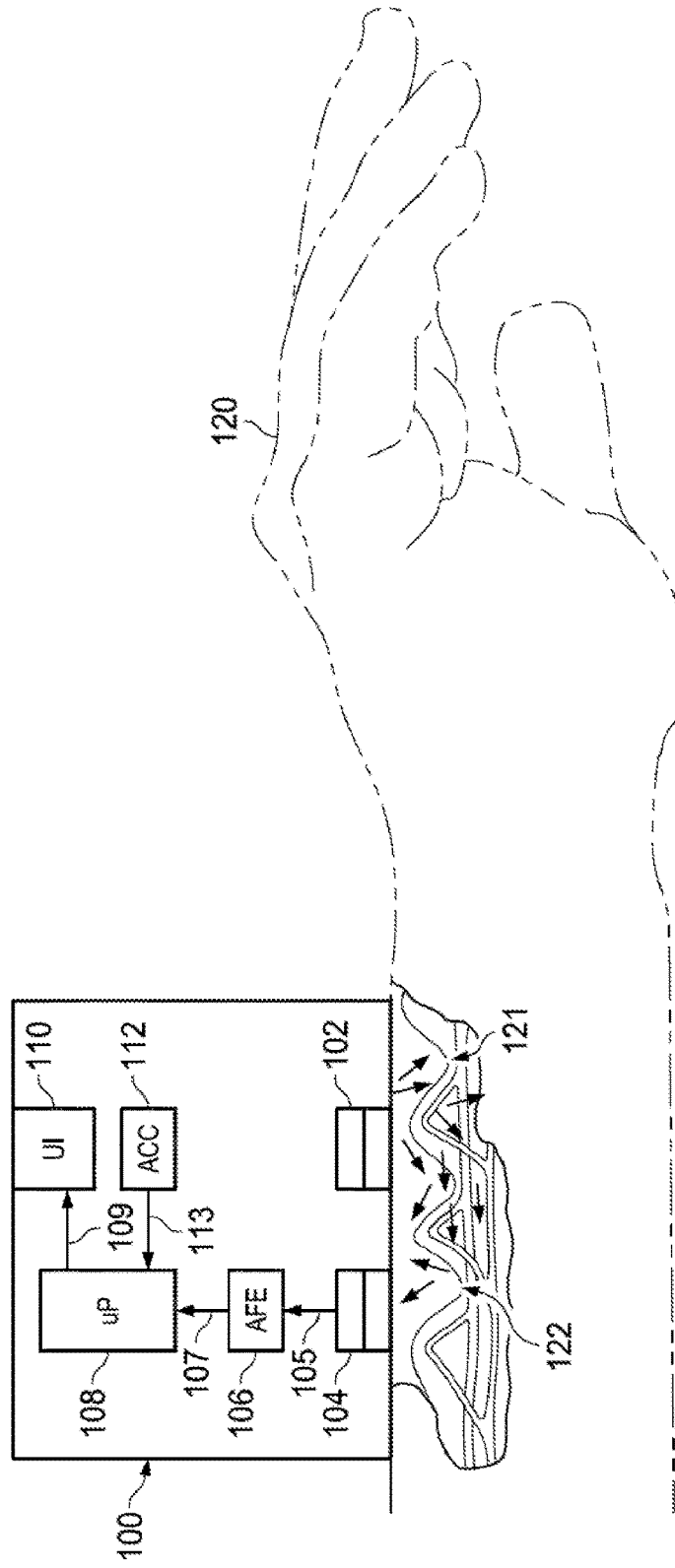
FIG. 1 is a partial schematic diagram of a system to measure reflected light from a patient's skin for estimating the patient heart rate.

In the drawings, like reference numerals refer to like elements throughout, and the various features are not necessarily drawn to scale. In the following discussion and in the claims, the terms "including", "includes", "having", "has", "with", or variants thereof are intended to be inclusive in a manner similar to the term "comprising", and thus should be interpreted to mean "including, but not limited to . . . "

Figure 2:
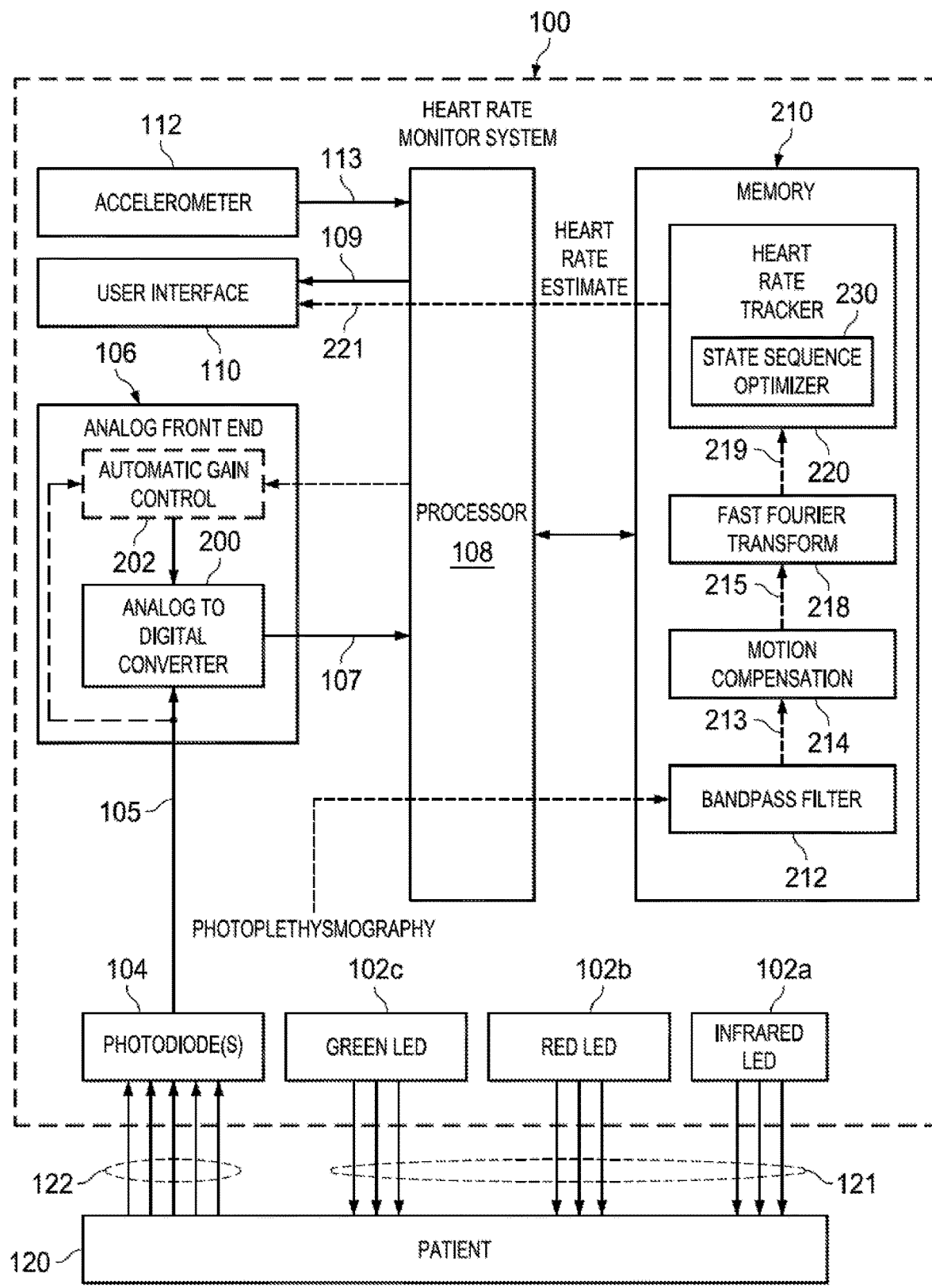
FIG. 2 is a detailed schematic diagram of an example heart rate estimation system using state sequence optimization.

Referring initially to FIGS. 1 and 2, FIG. 1 shows a wearable heart rate monitor system 100 to measure reflected light from the skin of a patient 120 to determine a heart rate estimate (HRE) value. FIG. 2 shows further details of the heart rate estimation system 100, including a processor implemented heart rate tracker 220 with a state sequence optimizer (SSO) 230. The system 100 estimates the patient heart rate by identifying heart rate hypotheses, or states, for a current time window according to digital sample values of a PPG signal or other pulsed signal for the current sample time window. The system 100 computes a rate change value for potential rate transitions between states of the current time window and the previous time window. The system 100 computes branch metric values for state transition pairs as a function of the rate change value and a frequency domain amplitude of the corresponding rate hypothesis for the current time window n, and determines the pulsed signal rate estimate according to a maximum path metric computed according to the branch metric value and a corresponding path metric value for the previous time window.

In one non-limiting pulsed signal rate estimation application, the system 100 is shown in FIG. 1 adjacent to a patient wrist for reflective PPG monitoring. In this example, the system 100 uses reflected light measurement techniques via one or more light sources (e.g., LED(s)) 102 and one or more optical sensors (e.g., photo diode(s)) 104. The light source 102 and the optical sensor 104 are disposed along a common plane in this example. Coplanarity of the light source 102 and the sensor 104 is not required in all implementations. In other examples, transmission configurations are possible, with a light source and a light sensor disposed on opposite sides of a patient's finger or other portions of a patient's body to assess light transmission and/or absorption for determining patient heart rate. The light source 102 in FIG. 1 directs a first light signal 121 toward the skin of the patient 120. The first light signal 121 in this example is reflected in the patient 120 with some measure of absorption, and a reflected second light signal 122 is generated. The optical sensor 104 detects the second light signal 122 from the patient 120. In this example, the sensor 104 generates an analog PPG signal 105 that represents reflection of the first light signal 121 in the patient 120. In other examples (not shown) where the sensor 104 and the source 102 are on opposite sides of the patient's finger, the sensor 104 provides a PPG signal 105 that represents transmission or absorption of light through the patient. In one example, a single light source 102 and a single optical sensor 104 are used. The example of FIG. 2 incldes multiple LED light sources 102a-102c that provide corresponding first light signals 121 at different wavelengths. The first light source 102a in this example provides infrared (IR) light 121, the second source 102b provides red light 121, and the third optical source 121c provides green light 121.

The system 100 further includes an analog front end (AFE) circuit 106. One or more optical sensors 104 receive the second light signal 122, and provide one or more PPG signals 105 to the AFE circuit 106. The AFE circuit 106 includes suitable analog signal conditioning circuitry (not shown) to receive and condition the PPG signal or signals 105, as well as an analog to digital converter (ADC) 200. The ADC 200 samples the PPG signal 105 and generates a plurality of digital PPG sample values 107 in a first time window for use in estimating the patient heart rate corresponding to the time window. The system 100 in one example operates in continuous fashion to continually monitor received PPG signals 105 and to estimate the patient heart rate based on an integer number of samples in individual ones of a series of multiple time windows to yield a heart rate estimate (HRE) value for each corresponding time window.

The ADC 200 operates at a fixed or adjustable sample rate, and the time windows in certain examples include a sufficient number of samples to characterize the PPG signal 105 over multiple heartbeats of the patient 120. For example, the length of the time windows W in one example is on the order of 8-10 seconds. The time windows in one example are of equal length, but other embodiments can have time windows of different lengths. The AFE circuit 106 in FIG. 2 also includes an analog automatic gain control (AGC) circuit 202 to adjust the gain of the signal 105 converted by the ADC circuit 200. In certain examples, the AGC circuit 202 receives the signal or signals 105 and dynamically adjusts an input buffer amplifier gain to provide a signal for conversion by the ADC circuit 200. In some examples, the analog AGC circuit 202 may also receive an external control signal or value from a processor 108 to set the gain for conversion of the PPG signal or signals 105 based on digital automatic gain control (DAGC) operation in the digital domain on previously received samples. In addition, the system 100 may include an accelerometer 112 providing a signal 113 to the processor 108.

The ADC 200 provides digital sample values 107 of the PPG signal to the processor 108 and an associated electronic memory 210 for digital processing to estimate the patient heart rate. The processor circuit 108 can be any suitable digital logic circuit, programmable or pre-programmed, such as an ASIC, microprocessor, microcontroller, FPGA, etc. that operates to execute program instructions stored in the electronic memory 210 to implement the features and functions described herein as well as other associated tasks to implement a monitor system 100. In certain examples, moreover, the memory circuit 210 can be included within the processor circuit 108. The processor 108 in the examples of FIGS. 1 and 2 includes an interface connection 109 to a user interface (UI) 110, such as a display (not shown). In certain examples, the memory 210 constitutes a non-transitory computer-readable storage medium that stores computer-executable instructions that, when executed by the processor 108, perform the various features and functions detailed herein.

In the example of FIG. 2, the processor 108 implements instructions corresponding to various functions or components 212-220 in the memory 210, including a filter component (bandpass filter or BPF) 212, a motion compensation component 214, a Fast Fourier Transform (FFT) component 218 and a heart rate tracker (HRT) component 220 with a state sequence optimizer 230. In operation, the processor 108 implements the functional components 212-230 to operate on the received PPG samples 107 to provide a heart rate estimate value (HRE) 221, which can then be provided to the user interface (UI) 110, such as a display to render the HRE value 221 to a patient 120.

The processor 108 implements the filter component 212 to filter the digital PPG sample values 107 to generate a plurality of filtered values 213 corresponding to the first time window W1. The processor 108 implements low pass filtering by the filter component 212 to remove certain motion artifacts or other low frequency components not related to the patient heart rate. In the illustrated example, the processor 108 executes the instructions of the component 212 to implement bandpass filtering to also remove high-frequency noise components. As previously discussed, the methods and systems of the present disclosure can be used for estimating a rate of any pulsed signal. Although described herein in the context of a pulsed PPG signal 105 heart rate estimation, the various concepts can be employed with any pulsed signal. The processor 108 in the illustrated example performs motion compensation processing on the filtered values 213 to generate a plurality of motion compensated values 215 corresponding to the first time window n. In one example, the motion compensation component 214 implements any suitable motion compensation algorithms or processing, including spectrum subtraction, compressed sensing with signal decomposition, and/or normalized least means squared or NLMS processing.

Following motion compensation, the processor 108 provides implements the FFT component 218 and the HRT component 220 in order to determine the heart rate estimate HRE value 221 representing the heart rate of the patient 120 for the current time window n according to the frequency content of the motion compensated values 215. In one example, the processor computes the frequency content of the motion compensated values 215 using a Fast Fourier Transform FFT algorithm via the instructions of the component 218 in order to generate a frequency spectrum including frequency component values 219. The processor 108 implements the heart rate tracking component 220 in this example to determine the HRE value 221 according to discernible peaks in the frequency spectrum data 219 via the state sequence optimizer component 230.

Figure 3:
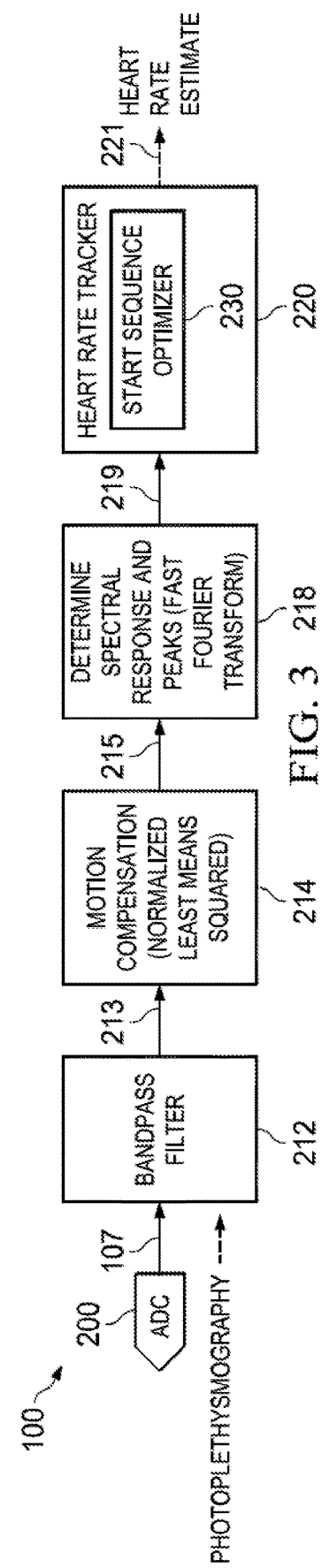
FIG. 3 is a schematic diagram of a heart rate estimation example for processing a single light signal in the system of FIGS. 1 and 2.

FIG. 3 illustrates the digital domain processing for a single PPG light signal 105 in the system 100 of FIGS. 1 and 2 as described above. In other examples, multiple light signals 105 can be processed using the components 212-220, for example, based on first light signals 121 generated by light sources 102 of different wavelengths (e.g., infrared or IR, red, green, etc.). The system 100 in this example may include a corresponding set of multiple optical sensors (e.g., photodiodes) 104, each receiving a corresponding light signal 122 and generating a corresponding second analog PPG signal 105 representing transmission or reflection in the patient 120. For example, the first optical sensor 104 detects the second light signal 122 representing transmission or reflection of the first light signal 121 from the first light source 102a, and the processor 108 operates on sampled values in a first signal processing chain associated with the first wavelength. For an additional light source 102b and an associated second optical sensor 104, the analog PPG signal 105 corresponds to a detected fourth light signal 122 representing transmission or reflection of a third light signal from the second source 102b, and the processor 108 forms filtering and motion compensation (and possibly gain adjustment) in a second digital signal processing chain.

Figure 4A:
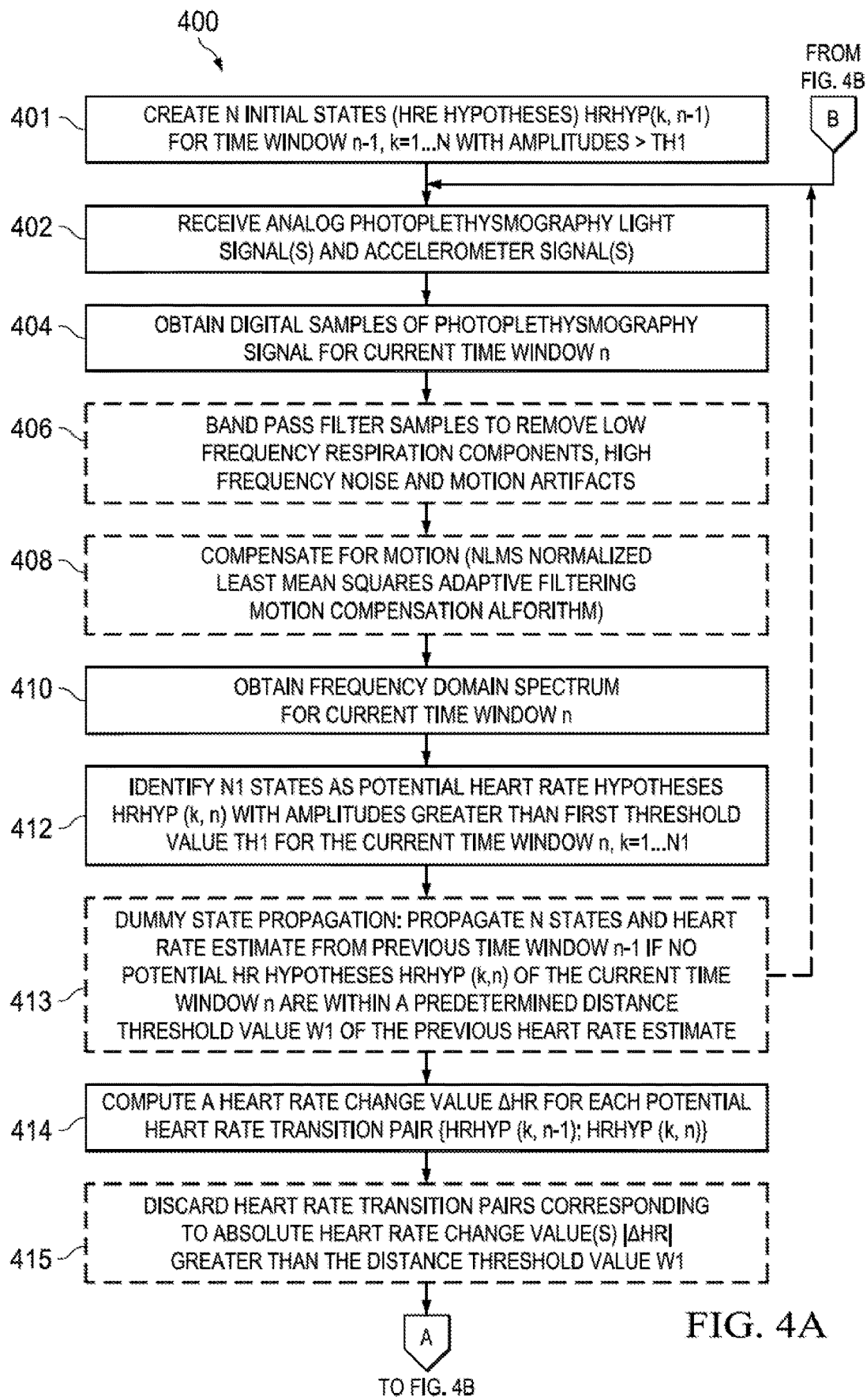
FIGS. 4A and 4B show a flow diagram of a method to estimate the heart rate of a patient.
Figure 4B:
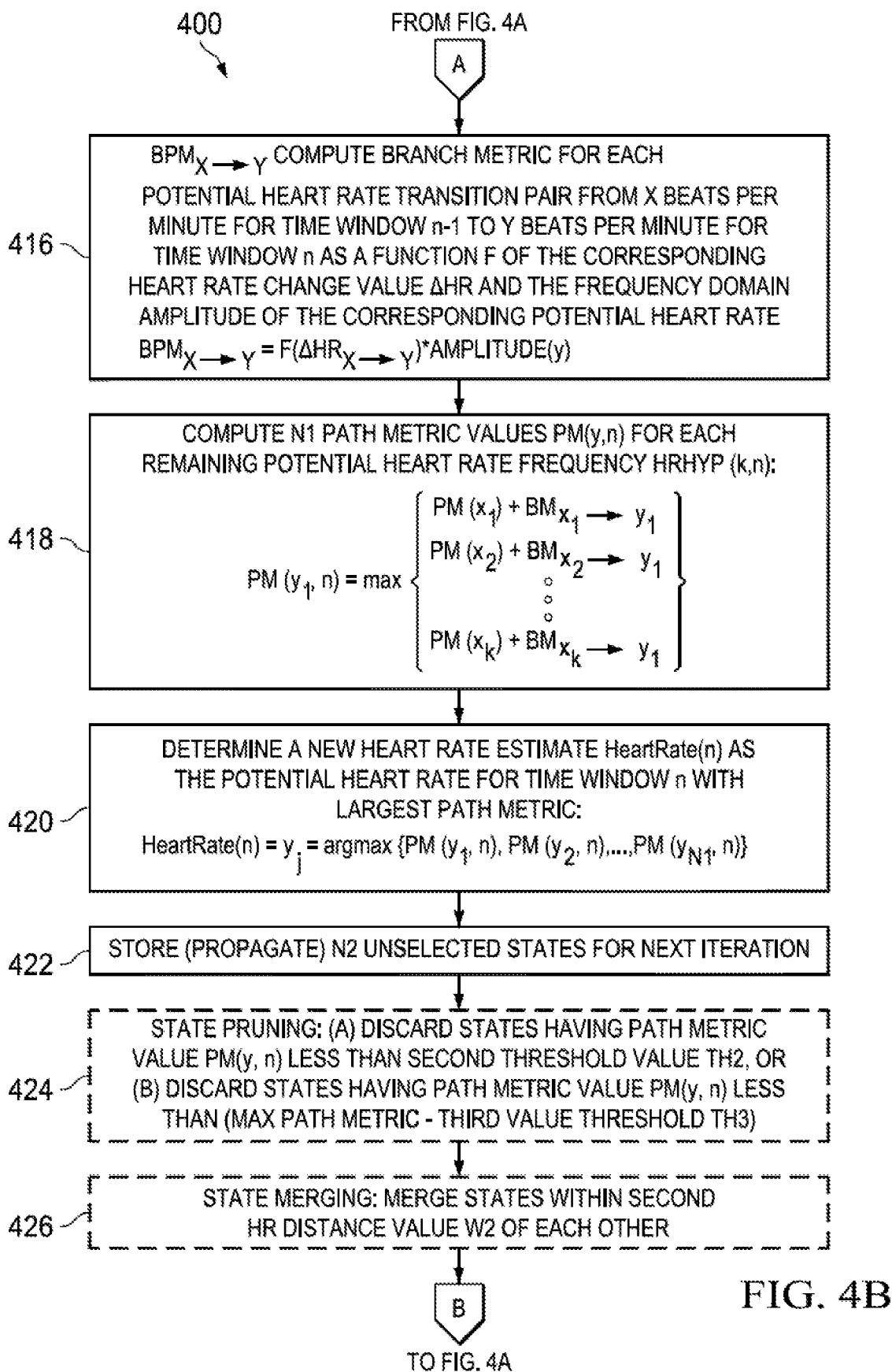

FIGS. 4A and 4B provide a flow diagram of a method 400 to estimate a rate of a pulsed signal. In the general case, the method 400 can be implemented in any suitable processing system. In one example, the processor 108 of the heart rate monitor system 100 is programmed by instructions in the memory 210 in order to implement the method 400 to estimate a patient heart rate based on a pulsed PPG signal 105, and the method 400 as described below in the context of this example application. In other implementations, the process 400 can be implemented in a general purpose computer (not shown), in a medical equipment processor, or other processing circuit or system. The processor 108 of the heart rate monitor system 100 generally implements the method 400 in continuous fashion, providing a heart rate estimate at each of a series of sample time windows.

As shown in FIG. 4A, the processor 108 begins executing the state sequence optimizer (SSO) component 230 (e.g., at power up) to characterize an initial frequency domain spectrum of the PPG signal input by creating an integer number N initial states corresponding to a time window n−1. In this initial or training phase, the SSO 230 may be initialized to a maximum of N heart rate hypotheses or states, that have amplitudes in the frequency domain greater than a first threshold value for the time window n−1. In some embodiments, the initial heart rate hypotheses may correspond to the largest N distinct spectral peaks whose amplitude is above a first threshold TH1A. For each heart rate hypothesis, a corresponding path metric is assigned and the metric may simply be the spectral amplitude. In one example, the processor 108 sets the initial path metric to the spectral amplitude normalized by a scaling factor. Since the heart rate typically includes second and third harmonics, in an alternative embodiment an initial search window may first be defined e.g., [30 BPM-250 BPM], and the initial N heart rate hypotheses correspond to the N largest distinct peaks in the search window that have second and third harmonics above a threshold TH1B. Alternatively, the N hypotheses may correspond to the N heart rates hypotheses in the initial search window with the largest metric, where the metric is the sum of fundamental spectral peak, second harmonic peak and third harmonic peak.

At 402 in FIG. 4A, the iterative heart rate estimation processing starts with the analog front end circuit 106 receiving one or more analog PPG light signals. In certain examples, accelerometer signals are also received at 402. At 404, digital samples are obtained of the analog PPG signal over a corresponding current time window n, for example, using an ADC circuit 200 as described above. At 406, the digital PPG samples of the current time window n are filtered, for example, by execution of digital filtering program instructions 212 by the processor 108 described above. At 408, the filtered samples are motion compensated. In one example, the motion compensation at 408 is implemented using NLMS adaptive filtering or other suitable algorithm by processor execution of the compensation component instructions 214 above to provide motion compensated values 215. As discussed above, the method 400 can be used for other pulsed signals, and the filtering and motion compensation steps at 406 and 408 can optionally be omitted.

Figure 5:
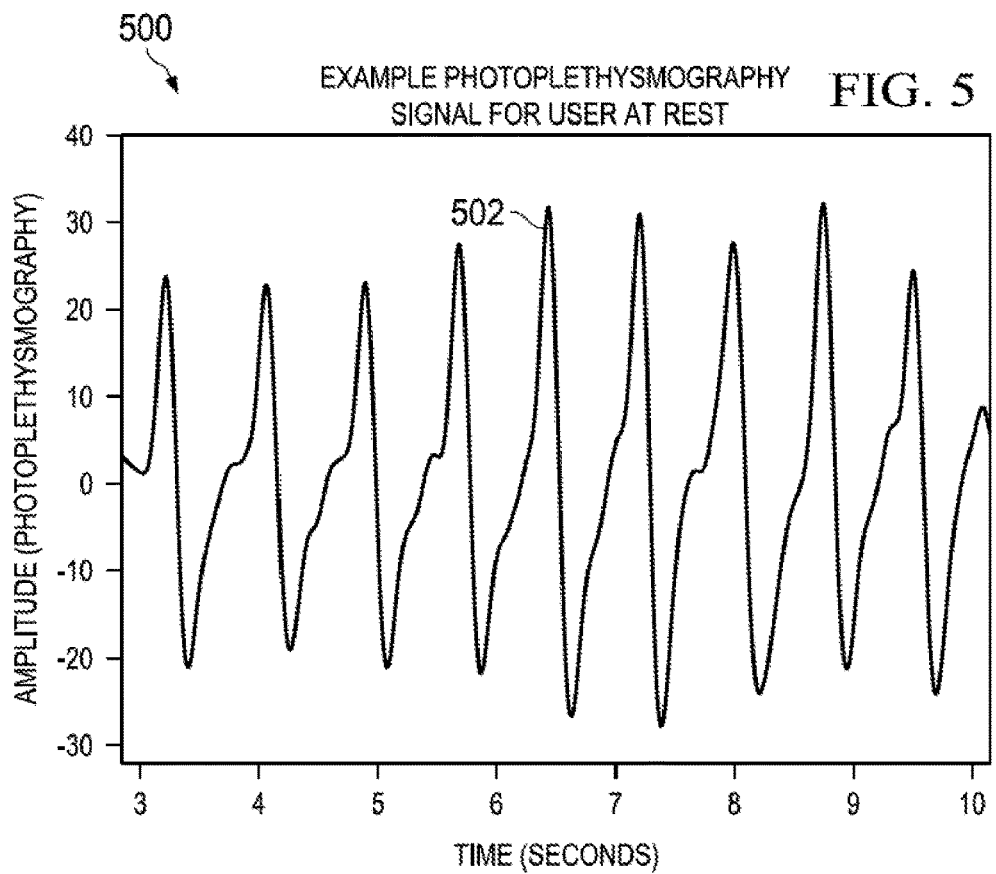
FIG. 5 is a signal diagram of a time domain filtered PPG signal.
Figure 6:
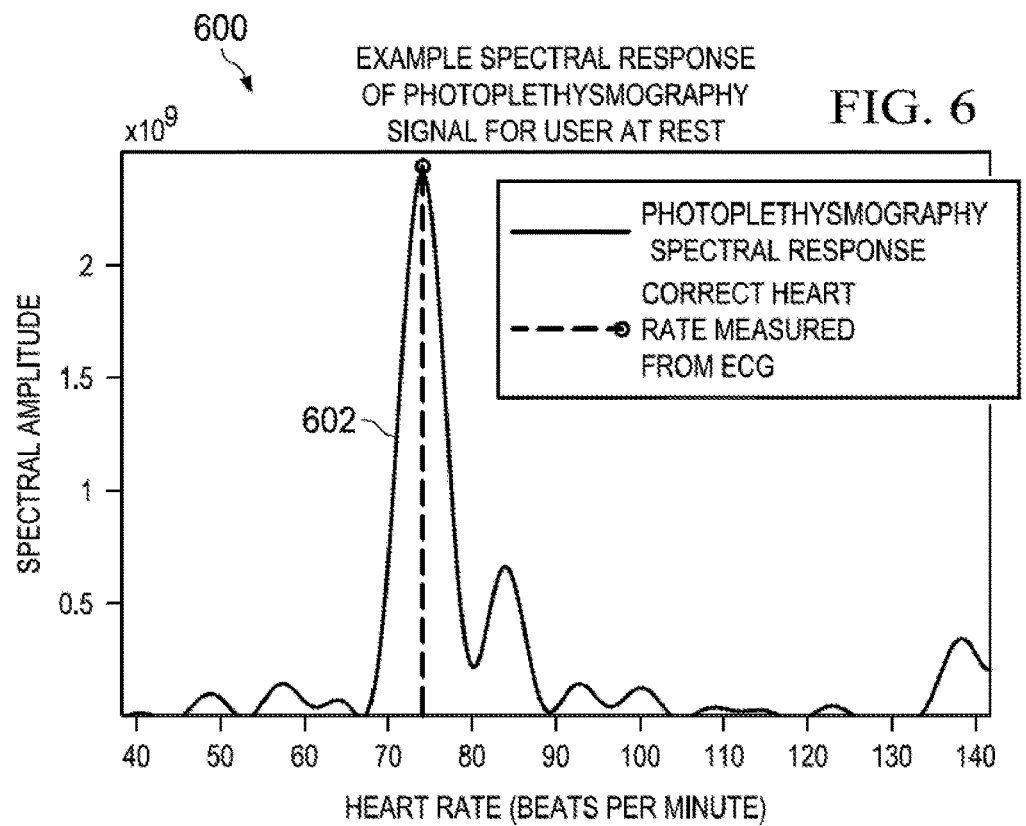
FIG. 6 is a signal diagram of a frequency domain filtered PPG signal corresponding to the time domain signal of FIG. 5 showing a single dominant peak corresponding to an actual patient heart rate.

Referring briefly to FIGS. 5-8, a signal diagram 500 and FIG. 5 shows a pulsed or oscillating time domain filtered PPG signal 502, and the diagram 600 and FIG. 6 shows a corresponding frequency domain filtered PPG signal 602 with a single dominant peak (e.g., at approximately 73 bpm) corresponding to an actual patient heart rate. PPG based heart rate estimation during motion is sometimes difficult due to motion artifacts in the PPG signal. This problem can be addressed, to a certain extent, using one or more motion compensation algorithms (e.g., at 408 in FIG. 4A) and/or use of a heuristic based tracker to track the spectral peak. However, heuristic based trackers require multiple FFTs, and thus are undesirable for low complexity implementations. In addition, heuristics for tracking the spectral peak do not provide a structured approach for candidate tracking. The state sequence optimizer 230 in the system 100 advantageously provides heart rate tracking that makes prior use of how the heart rate evolves over time, and inherently tracks potential solutions by associating a metric with the heart rate estimate that depends on the current time window n as well as history from one or more prior time windows n−1. In this regard, and a patient is at rest and there are no motion artifacts, the heart rate can be easily inferred from the PPG signal through either counting the zero-crossings or keeping track of the peaks and valleys. Thus, at rest, the dominant spectral component also corresponds to the heart rate as shown in FIG. 6. However, the PPG signal typically includes motion artifacts when the patient is not at rest. For example, if a watch containing the optical heart rate system 100 is not tied tightly to the patient's wrist, the watch moves when the user is in motion. In this case, the motion artifact effect is multiplicative. The additive components result in new peaks in the spectral signature while the multiplicative effect results in a spectral spreading (multiplication in time is convolution in frequency) of the heart rate signature i.e., presence of new peaks.

Figure 7:
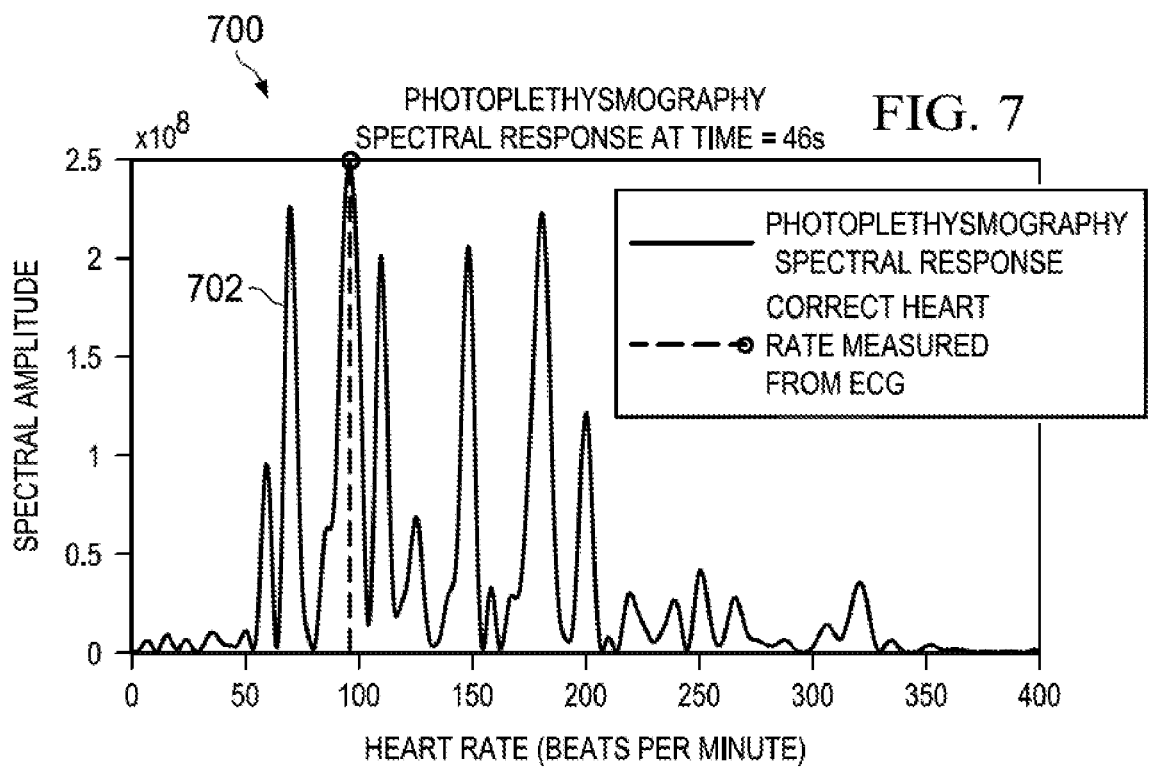
FIG. 7 is a signal diagram of a frequency domain PPG signal spectrum at a first time when a dominant frequency domain peak corresponds to the correct patient heart rate.
Figure 8:
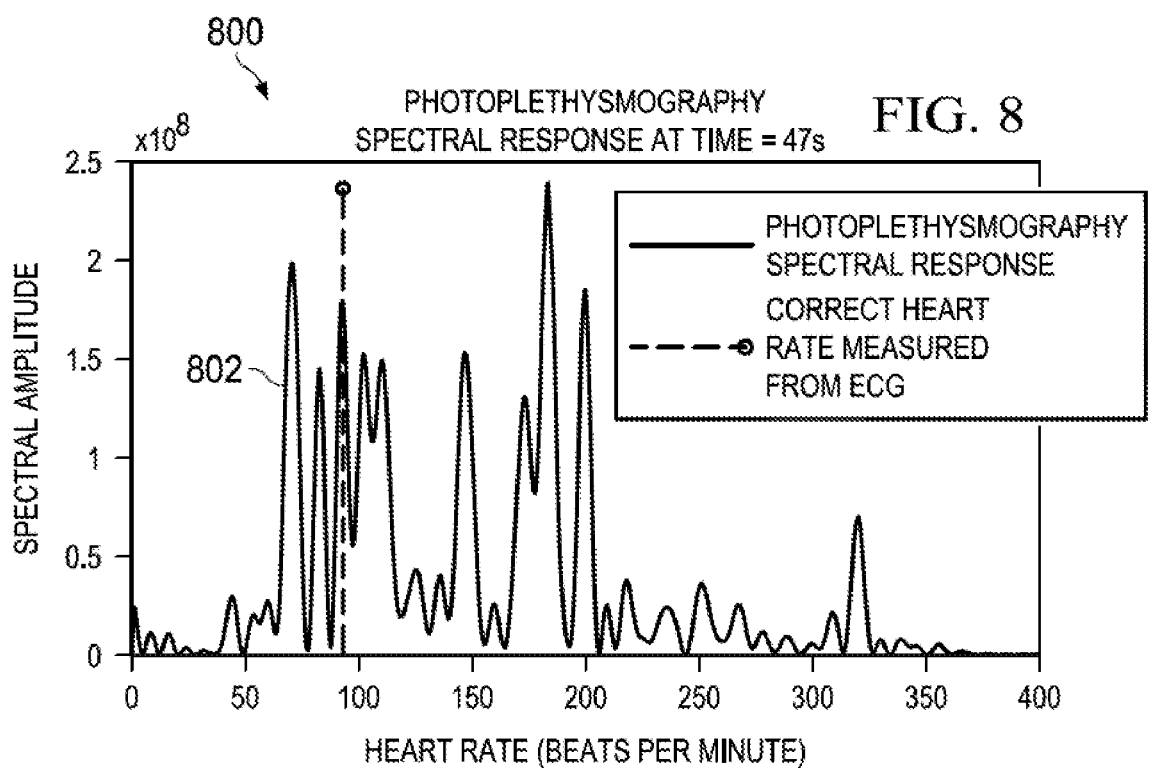
FIG. 8 is a signal diagram of a frequency domain PPG signal spectrum at a second time when the dominant frequency domain peak does not correspond to the correct patient heart rate.

Referring also to FIGS. 7 and 8, absent perfect motion compensation and a perfect deconvolution of the multiplicative artifacts, it is difficult to minimize the motion induced spectral peaks. Importantly, the maximum peak may not always correspond to the correct heart rate even after motion compensation processing. In addition, as the patient motion changes over time, this inaccuracy in peak tracking also changes over time. A signal diagram 700 and FIG. 7 illustrates a frequency domain PPG signal spectrum 702 at a first time when a dominant frequency domain peak corresponds to the correct patient heart rate. At a subsequent sample time window, a signal diagram 800 in FIG. 8 shows the frequency domain PPG signal 802 when the dominant frequency domain peak does not correspond to the correct patient heart rate. As seen in FIG. 8, at any given time window, there may also be several spectral peaks that have similar amplitude to the spectral peak that corresponds to the correct heart rate. However, as the motion component in the PPG signal is typically a non-stationary process, there is a higher likelihood of the dominant spectral peak or a set of the dominant spectral peaks to correspond to the correct heart rate. Furthermore, the heart rate change from one time instant to the next cannot arbitrarily jump by a large amount i.e., it follows a certain distribution.

Returning to FIG. 4A, the heart rate monitor system processor 108 implements the state sequence optimization component 230 in which each candidate heart rate is considered as a possible state and is assigned a probability or a path metric. The path metric preferably captures the history of the previous heart rate estimate(s), and captures the rate of change of the heart rate from the previous heart rate estimate. Processor execution of the SSO component 230 in the illustrated example uses the spectral response of the motion compensated PPG signal as an input. In general, the processor execution of the SSO component 230 creates the initial heart rate hypothesis based on the spectral amplitudes and assigns a metric to each hypothesis, and at each time step or sample time window, computes branch metrics (416 in FIG. 4B) from the heart rate hypothesis for time window n−1 to those for time window n. The process 400 also includes computing or updating a path metric at 418 for the heart rate hypothesis, and determines a new heart rate estimate for the current time window n at 420 representing the patient heart rate as the heart rate hypothesis having a maximum candidate path metric value. The SSO component 230 in certain examples also selectively provides dummy state propagation at 413 to carry a previous set of states forward where a subset of the most probable heart rate hypothesis for time window n−1 have no valid heart state to jump to in time window n, and may also optionally implement state pruning and state merging at 424 and 426 in FIG. 4B as discussed further below.

Figure 9:
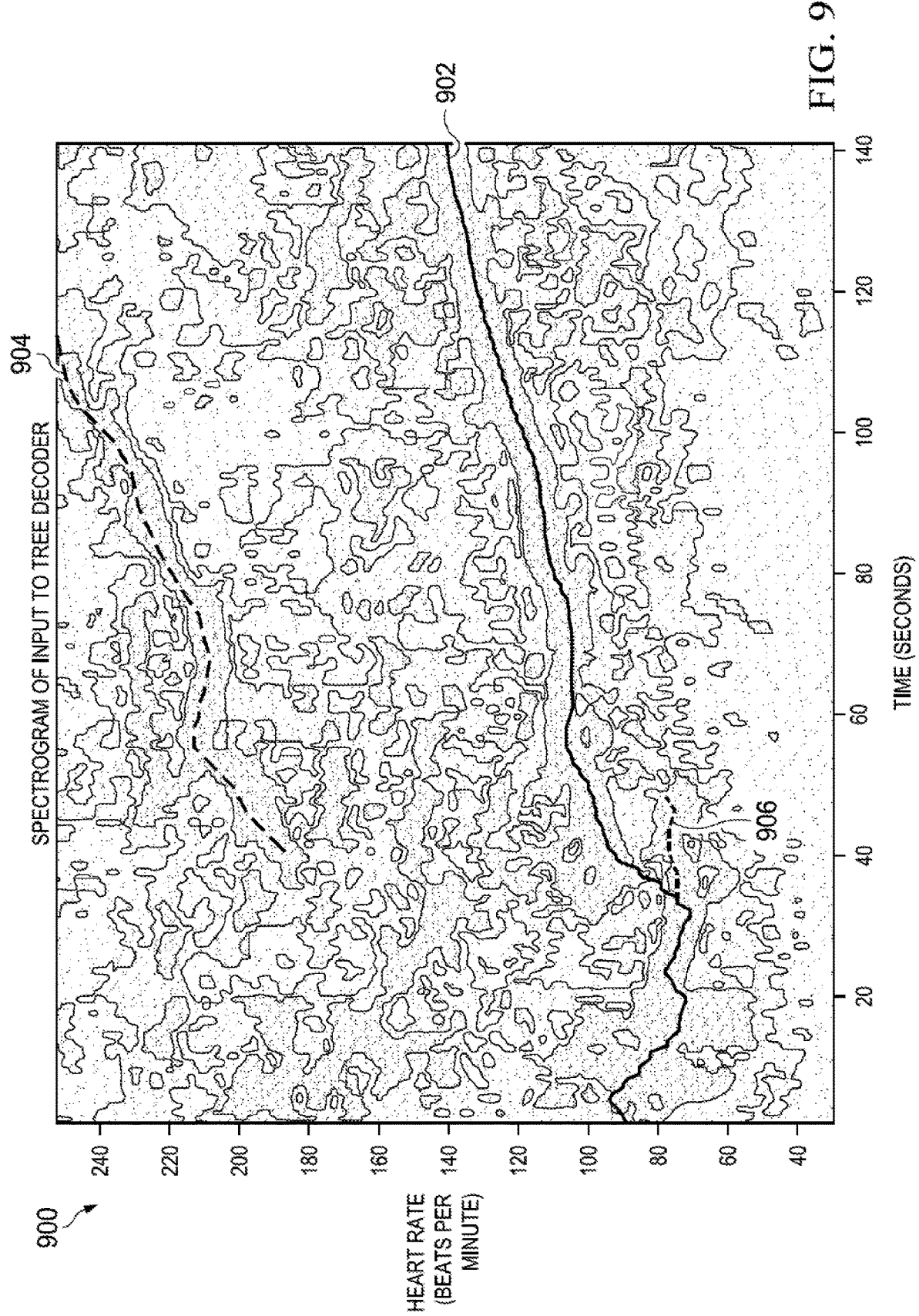
FIG. 9 is a short-term spectrogram showing frequency domain intensity for different heart rates over time, including a true patient heart rate tracking curve as well as alternate heart rate state tracks.
Figure 10:
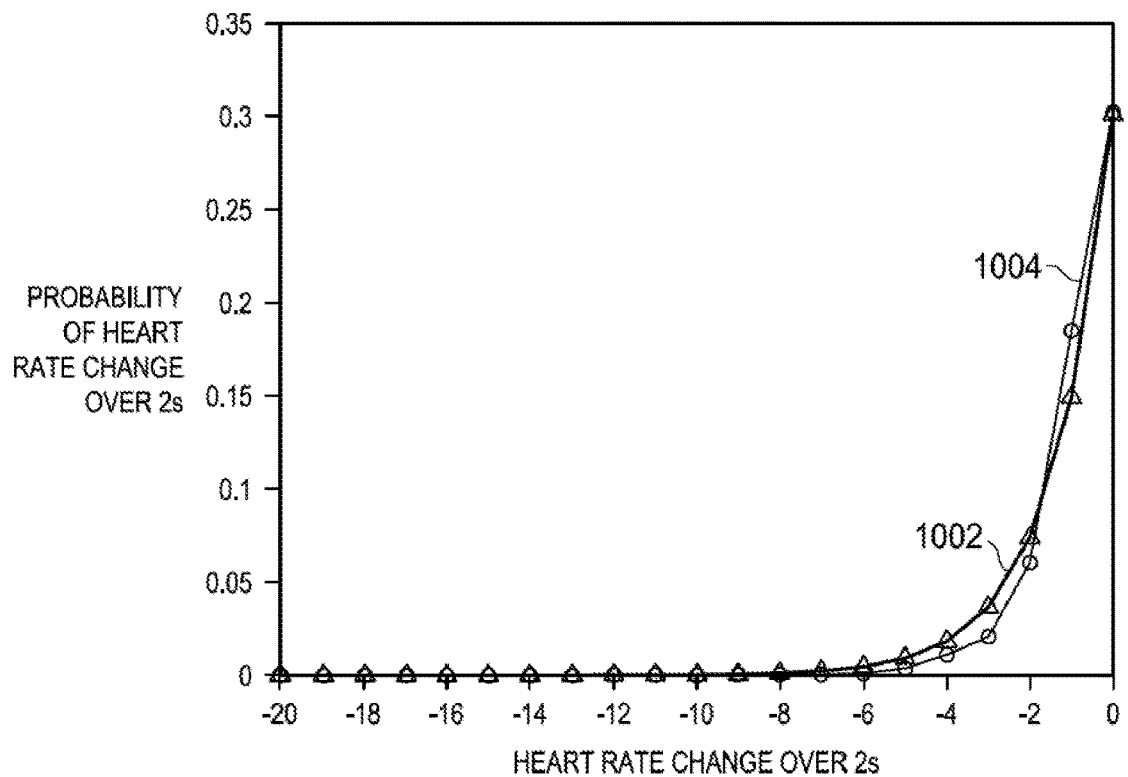
FIG. 10 is a graph of actual and modeled probability density function curves for decreasing or negative heart rate changes.
Figure 11:
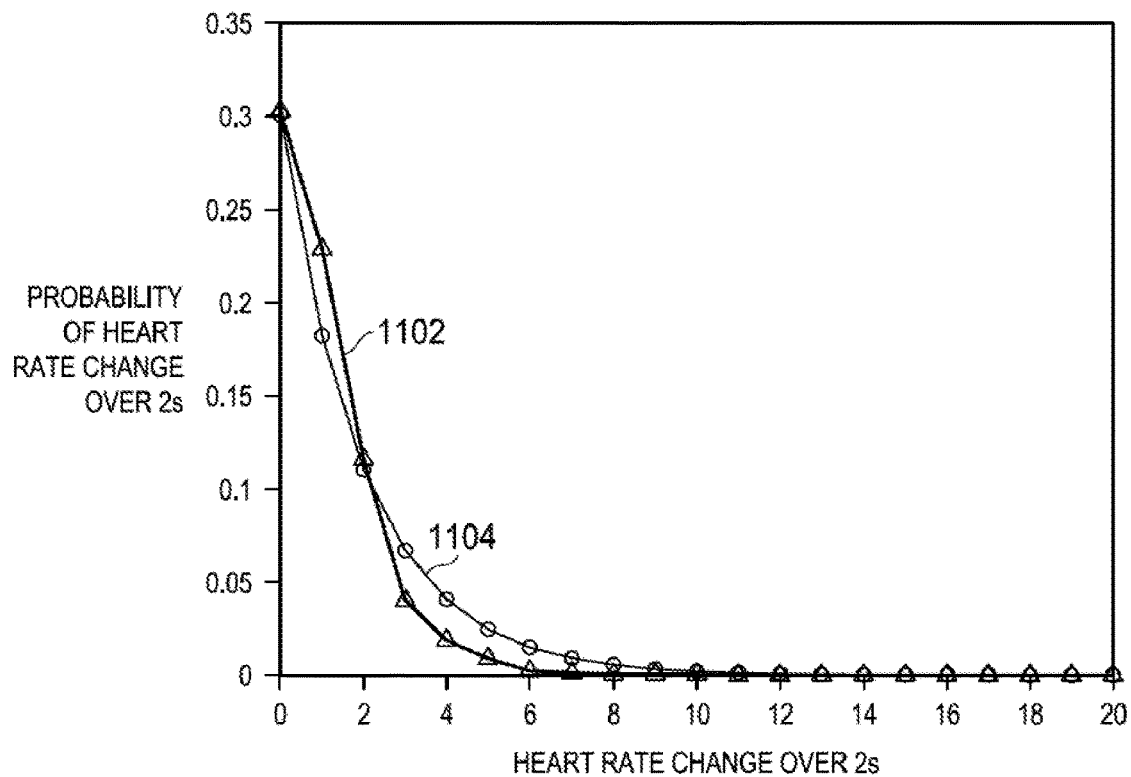
FIG. 11 is a graph of actual and modeled probability density function curves for increasing or positive heart rate changes.
Figure 12:
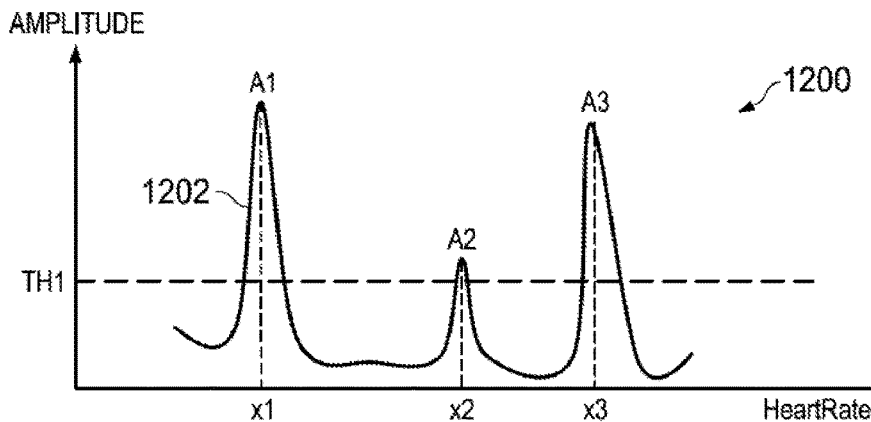
FIG. 12 is a signal diagram of a frequency domain PPG signal spectrum at a first time including three frequency domain peaks above a threshold.
Figure 13:
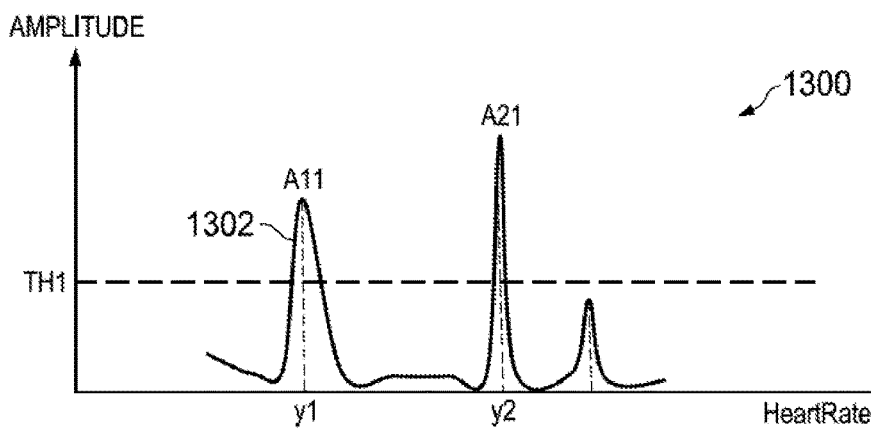
FIG. 13 is a signal diagram of a frequency domain PPG signal spectrum at a second time including two frequency domain peaks above the threshold.
Figure 14:
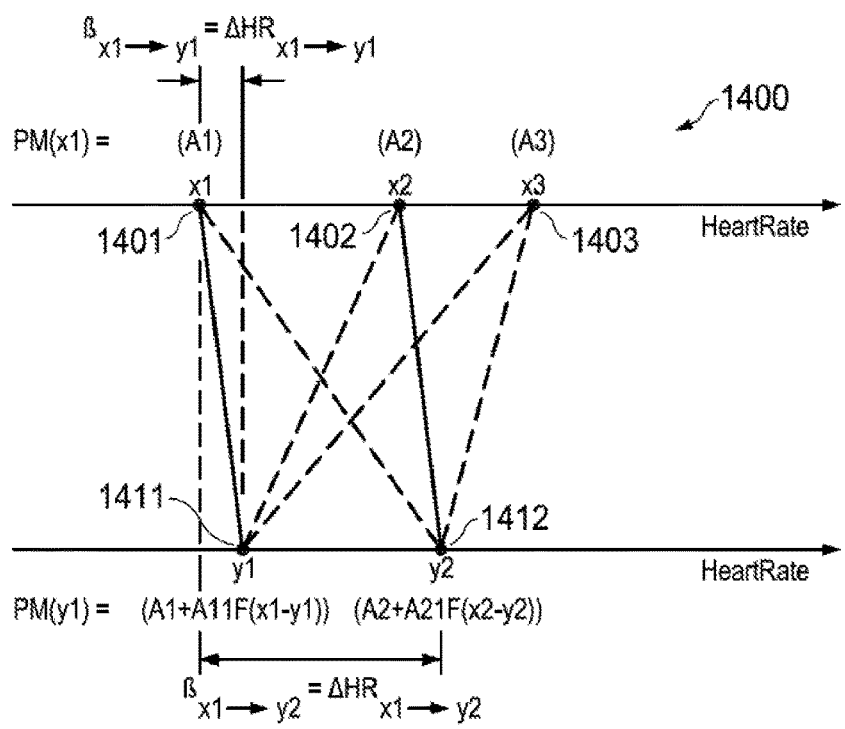
FIG. 14 is a heart rate transition diagram showing possible transitions from the three states at the first time in FIG. 12 to the two states at the second time in FIG. 13.

Referring also to FIGS. 9-14, operation of the state sequence optimizer component 230 is illustrated and described with respect to a simplified example using PPG signals for heart rate estimation. FIG. 9 shows a short-term spectrogram diagram 900 that includes frequency domain intensity for different heart rates (in beats per minute or bpm) over time, including a true patient heart rate tracking curve 902 as well as alternate heart rate state tracks 904 and 906. FIG. 10 shows a graph 1000 of actual and modeled probability density function curves 1002 and 1004, respectively for decreasing or negative heart rate changes. A graph 1100 in FIG. 11 shows curves 1102 and 1104 respectively representing actual and modeled probability density function curves for increasing or positive heart rate changes. FIGS. 10 and 11 illustrate monotonically decreasing probability density functions (PDFs) representing the decreasing probability that a patient heart rate will change by large amount within a given timeframe (e.g., two seconds in the illustrated examples). FIG. 12 illustrates a frequency domain PPG signal spectrum 1200 as a curve 1202 at a first time including three frequency domain peaks of amplitude A1, A2 and A3 at corresponding heart rates or frequencies x1, x2 and x3 above a first threshold value TH1. In one example, the spectrum 1200 of FIG. 12 represents PPG sample data from a previous sample time window n−1. FIG. 13 illustrates a subsequent frequency domain PPG signal spectrum as a curve 1302 at a current time window n including two frequency domain peaks at heart rates y1 and y2 having corresponding amplitudes A11 and A21 above the threshold TH1. The state sequence optimizer component 230 and the process 400 are described hereinafter with respect to the examples of FIGS. 12 and 13 for updating state transition path metrics to estimate a current patient heart rate, where FIG. 14 provides a heart rate transition diagram 1400 showing possible transitions from the three states 1401, 1402 and 1403 at the time window n−1 in FIG. 12 to the two states 1411 and 1412 at the current time window n in FIG. 13.

The state sequence optimization processing begins at 410 in FIG. 4A. At 410, the processor 108 obtains a frequency domain spectrum for the current time window n. In one example, the processor computes the frequency content of the motion compensated values 215 using a Fast Fourier Transform FFT algorithm at 410 to generate 410 a frequency domain spectrum for the current time window n according to the digital PPG sample values 107. At 412, the processor 108 identifies a plurality N1 of states for the current time window n as heart rate hypotheses HRHYP (k, n) having amplitudes in the frequency domain spectrum greater than a first threshold value TH1 for the current time window n. A kth two-tuple (HRHYP(k,n−1), PM(k,n−1))k denote the kth heart rate hypothesis (HRHYP(k,n−1)) at time window n−1 with a path metric equal to PM(k,n−1). At the current time window n, the spectral response of the motion compensated PPG signal is determined at 410.

At 412, the set of N1 heart rate hypotheses are identified from the spectral response whose amplitudes are largest and are distinct peaks i.e., [(HR(1,n), Amp(1,n)), (HR(12,n), Amp(2,n)), . . . , (HR(N1,n), Amp(N1,n)). In one example, the spectral input is computed by an FFT on the motion compensated PPG signal, and the distinct peaks of amplitudes A11 and A12 in FIG. 13 are found by looking for all local maxima that are above the threshold TH1. The spectral input may be normalized in various ways prior to comparing against a threshold. Several non-limiting examples include normalizing with respect to the maximum peak, normalizing with respect to the total power in the input signal, and normalizing with respect to a predefined constant. As noted at 412 in FIG. 4A, the SSO component 230 in certain examples provides an efficient implementation after an initial set of heart rate hypothesis are identified. For each heart rate hypothesis or state, the search space is within a distance threshold value +/−W1 heart beats from the previous HRE estimate value. In this example, the processor 108 computes the spectral response only around those frequencies. In one embodiment, the processor 108 implements this approach by the Goertzel algorithm. In another embodiment, this computation may be done by using the DFT itself.

At 413, the processor 108 optionally implements dummy state propagation, for example, for iterations of the process 400 in which no spectral peak is identified for time window n which is within the distance threshold W1 of the heart rate estimate for time window n−1. In this case, the processor 108 determines the HRE value 221 representing the heart rate of the patient 120 for the current time window n as the previous heart rate estimate HRE for the previous time window n−1. In addition, the processor 108 carries at least some of the heart rate hypotheses HRHYP (k, n−1) from the previous time window n−1 forward to the current time window n. In this regard, the number of hypotheses N from the previous time window n−1 may, but need not be, the same as the number of hypotheses N1 determined for the current time window n. In certain examples, where none of the spectral peaks are within the distance threshold W1, the heart rate estimate value 221 for time window n−1 is carried forward along with its path metric to time window n, and the top N2 candidates for time window n−1 with the largest path metric are carried forward.

At 414, the processor 108 computes a heart rate change value ΔHR for each of a plurality of potential heart rate transition pairs. As shown in FIG. 14, for example, arrowed lines represent individual heart rate transition pairs corresponding to a heart rate transition to one of the heart rate hypotheses HRHYP (k, n) for the current time window n from one of a plurality of heart rate hypotheses HRHYP (k, n−1) for a previous time window n−1. FIG. 14 illustrates two example heart rate change values $\Delta HR_{x1 \to y1} = \beta_{x1 \to y1}$ and $\Delta HR_{x1 \to y2} = \beta_{x1 \to y2}$ for potential transitions from the point x1 at the previous time window n−1 to the points y1 and y2 at the current time window n. In one implementation, the processor 108 selectively discards heart rate transition pairs at 415 which correspond to heart rate change values ΔHR that are greater than the predetermined distance threshold value W1. In this example, for each heart rate hypothesis at the current time window n, the processor 108 computes the heart rate change values ΔHR for all the heart rate hypotheses for time window n−1, and only retains the heart rate change values ΔHR that are less than a distance threshold W1 are considered as valid transitions according to the following formulas:

$$\Delta HR_{1 \to 1} = HRHYP(1, n-1) - HR(1, n);$$

$1 \to 1$ transition valid if $abs(\Delta HR_{1 \to 1}) < W1$ $$\Delta HR_{k \to 1} = HRHYP(k, n-1) - HR(1, n);$$

$k \to 1$ transition valid if $abs(\Delta HR_{k \to 1}) < W1$ $$\vdots$$

$$\Delta HR_{k \to N1} = HRHYP(k, n-1) - HR(N1, n);$$

$k \to N1$ transition valid if $abs(\Delta HR_{k \to N1}) < W1$

As an example, if a heart rate hypothesis for time window n is 70 BPM, and the distance threshold value W1 is set to 20 BPM, the processor 108 only considers the heart rate hypothesis at the previous time window n−1 which are between 50 BPM and 90 BPM as valid transitions to the heart rate hypothesis of 70 BPM at the current time window n.

Returning to 416 in FIG. 4B, the processor 108 computes branch metric values BMx→y for each of the remaining plurality of potential heart rate transition pairs as a function F of the corresponding heart rate change value AHR and the frequency domain amplitude AMPLITUDE(y) of the corresponding heart rate hypotheses HRHYP (k, n) for the current time window n. In one example, the processor 108 computes the branch metric BMx→y at 416 for each of the potential heart rate transition pairs as a product of the function F of the corresponding heart rate change value AHR and the frequency domain amplitude AMPLITUDE(y) of the corresponding heart rate hypotheses HRHYP (k, n) for the current time window n. In one implementation, for potential heart rate transition $\Delta HR_{x \to y}$, a heart rate hypothesis x at the previous time window n−1 is represented as HRHYP (x, n−1) to a heart rate hypothesis y for time window n HRHYP (y, n), the branch metric BMx→y is defined as $F(\Delta HR_{x \to y})$ *AMP(y). In this example, the weighting function F(.) assigns a probability weighting to the change in heart rate from x to y.

In one example, the weighting function F is a monotonically decreasing function of an absolute value of the corresponding heart rate change value |ΔHR|. One example is shown in FIGS. 10 and 11, in which the weighting function F is a monotonically decreasing exponential function of the absolute value of the corresponding heart rate change value |ΔHR|. An example is the weighting function $F(X) = \alpha * e^{(-\beta X)}$ for positive constants (α, β). In this regard, when a patient 120 is in motion, the change in heart rate on a second by second basis can be modelled as an exponentially distributed random variable $\Delta HR_{n-1 \to n}$ of the form $Prob(\Delta HR_{n-1 \to n} - X) = \alpha * e^{(-\beta X)}$, where X is the heart rate change between the previous time window n−1 and the current time window n and (α, β) are constants. In some instances, the constants (α, β) further depend on whether X is positive or negative as shown in FIGS. 10 and 11. In this regard, the function may not be bilaterally symmetrical with respect to 0 bpm. In addition, α and β may also be a function of the heart rate, water content in an individual, external temperature or other factors, and the system processor 108 can adapt these parameters or be programmed with different parameters for the weighting function. In some examples, the weighting function constants may also depend on the type of activity being performed. The processor is configured in certain examples to adapt the bandwidth of a heart rate search space according to patient activity, such as by selectively decreasing β if the patient is transitioning between low and high activity states and by selectively increasing β if the patient's activity state is constant. For instance, if an individual is transitioning from a stationary activity such as sitting down or standing to a higher intensity activity state such as running, the value of β may be smaller allowing for a larger probability weighting for a larger heart rate change. Alternatively, if the person is performing a similar activity for a longer duration of time, then the value of β may be made larger allowing a lower probability of heart change. Activity classification may be done with accelerometer in certain implementations. Note that β in the above example, is a variable that controls the bandwidth of the heart rate change search space, and can be adapted by the processor 108 for intelligent heart rate estimation according to the patient activity.

In some examples, the processor 108 implements a weighting function F of the form F(X)=mX+c, where c is a positive constant and m is a negative constant. In other examples F(X) may take the form of a multi-step indicator function according to the following form:

$$F(X) = \begin{cases} 1 & |X| < W11 \\ \beta_1 & W11 \le |X| < W22 \\ \beta_2 & W22 < |X| \end{cases}$$

where $\beta_2$ is less than $\beta_2$. At 418 in FIG. 4B, the processor 108 computes an updated path metric for each hypothesis at the current time window n by choosing the transition among all the heart rate hypotheses at the previous time window n−1 whose path metric+branch metric is largest. For example, the set {x1, x2, . . . , xk} denotes heart rate states from the previous time window n−1 which are within the distance threshold W1 from a potential heart rate state y1 of the current time window n. In this case, the processor 108 selects the potential path metric for the current time window state y1 according to the following formula:

$$PM(y_1, n) = \max \begin{cases} PM(x_1) + BM_{x_1 \to y_1} \\ PM(x_2) + BM_{x_2 \to y_1} \\ \vdots \\ PM(x_k) + BM_{x_k \to y_1} \end{cases}$$

In this manner, for each heart rate hypothesis HRHYP (k, n) for the current time window n, the processor 108 computes multiple individual candidate path metric values PM(xk, n) as a sum of a corresponding branch metric value BMx→y and the corresponding path metric value PM(xk, n) for the corresponding heart rate hypothesis HRHYP (k, n−1) for the previous time window n−1. Moreover, for each heart rate hypothesis HRHYP (k, n) for the current time window n, the processor 108 selects the maximum one of the plurality of individual candidate path metric values PM(xk, n).

At 420 in FIG. 4B, with the path metrics updated, the processor 108 then determines the heart rate estimate value 221 as the estimate or representation the heart rate of the patient 120 for the current time window n as the heart rate hypothesis HRHYP (k, n) having a maximum candidate path metric value PM(xk, n), for example, according to the following formula: HRE(n)=$y_j$=arg max{PM($y_1$,n), PM($y_2$, n), . . . ,PM($y_{N1}$,n)}. In some embodiments, if the heart rate estimate is significantly different from the previous estimates it may be incorporated on an extra smoothing filter whose inputs are the current heart rate estimate and previous heart rate estimates. The smoothing filter may be a low-pass filter or a median filter.

At 422, the processor 108 stores (e.g., probably gates) an integer number N of the unselected states for the next iteration, and thus preserves the state of the monitored signal rate in the memory 210 (FIG. 2) for use in the next iteration time window.

At 424 in FIG. 4B, the processor 108 in one example selectively discards one or more states for the current time window n having a low path metric value PM(xk, n), e.g., below a second predetermined threshold value TH2. In this manner, the processor 108 keeps only the top k candidates (with respect to path metric) and other states are discarded. In another example, states may also be removed at 424 for the current sample time window if their path metric is less than the maximum path metric minus a third predetermined threshold value TH3.

At 426, the processor 108 may also implement selective state merging. For example, where two heart rate states are within a predetermined distance threshold value W2 of each other for the current time window n, the processor 108 selectively merges two or more states for the current time window n. Thereafter, the process 400 returns to 402 in FIG. 4A for the next time window iteration. Thus, the system 100 provides a heart rate estimate value 221 in each time window based on the current measured frequency domain peaks as well as the history of more than one peak from the previous time window or windows as maintained by the state of the path metric values PM.

Returning to FIG. 9, the system 100 at approximately 40 seconds interprets the relatively similar heart rate frequency domain peaks of approximately 73, 91 and 184 beats per minute according to the path metric that takes the history of the PPG signal into account, and preferentially selects the illustrated true patient heart rate tracking curve 902, even if the much higher heart rate peak is significantly higher than that of the true estimate, since this estimate aligns more closely with the prior history of the patient's heart rate based on the path metric values from the previous time window. As described above, the system 100 constructs the path metric as a function of the dominant spectral amplitudes and the rate with which they change over time. The method 400 and the system 100 in certain examples can also take into account the human dynamics of heart rate change based on activity type, for example, by allowing programming and/or adaptive modification of the weighting function coefficients and constants. The system 100 in certain examples also provides a low complexity solution, e.g., for consumer products to provide a heart rate estimate to a user (e.g., sports watches, wearable health indicator devices, etc.) for a reduced complexity implementation where the spectral response for only a discrete set of frequencies needs be computed.

Modifications are possible in the described embodiments, and other embodiments are possible, within the scope of the claims.

What is claimed is:

1. A method comprising:
   generating first samples for a first time window of a signal;
   generating second samples for a second time window of the signal, the second time window after the first time window;
   determining a first frequency domain spectrum using the first samples;
   determining a second frequency domain spectrum using the second samples;
   determining first pulse rates for the first time window based on the first frequency domain spectrum;
   determining second pulse rates for the second time window based on the second frequency domain spectrum; and
   determining a third pulse rate based on the first pulse rates and the second pulse rates.

2. The method of claim 1, further comprising:
   determining differences between the first pulse rates and the second pulse rates;
   determining transition pairs by pairing each one of the first pulse rates with a respective one of the second pulse rates;

determining a metric of each transition pair based on a difference between the one of the first pulse rates and the one of the second pulse rates of the transition pair;

ranking at least some of the transition pairs based on the metrics; and selecting one of the second pulse rates of one of the transition pairs as the third pulse rate based on a result of the ranking.

3. The method of claim 2, wherein the metric includes a component that decreases as the differences increase.

4. The method of claim 3, wherein the metric includes a component that reflects an activity state of an object, and the third pulse rate is of the object.

5. The method of claim 2, further comprising:
filtering the first samples and the second samples to generate, respectively, filtered first samples and filtered second samples;
performing motion compensation processing on the filtered first samples and the filtered second samples to generate, respectively, first motion compensated values and second motion compensated values; and
determining the first frequency domain spectrum based on performing a first Fourier transform operation on the first motion compensated values; and
determining the second frequency domain spectrum based on performing a second Fourier transform operation on the second motion compensated values.

6. The method of claim 2, wherein the differences are first differences, and the metric includes a component that reflects a second difference between the one of first pulse rates of the one of the transition pairs and a fourth pulse rate in a third time window prior to the first time window.

7. The method of claim 2, further comprising:
excluding a first transition pair of the transition pairs from the ranking based on the difference between one of the first pulse rates and one of the second pulse rates of the first transition pair exceeding a threshold.

8. The method of claim 2, further comprising:
excluding a first transition pair of the transition pairs from the ranking based on the metric of the first transition pair being below a threshold.

9. The method of claim 8, wherein the threshold is based on a maximum metric among the metrics of the transition pairs.

10. The method of claim 1, wherein determining first pulse rates based on the first frequency domain spectrum includes identifying first frequency components from the first frequency domain spectrum based on a prior pulse rate for a prior time window; and
wherein determining second pulse rates based on the second frequency domain spectrum includes identifying second frequency components from the second frequency domain spectrum based on the prior pulse rate.

11. The method of claim 1, wherein:
the signal represents a photoplethysmogram signal.

12. The method of claim 1, wherein:
the third pulse rate represents a heart rate.

13. A non-transitory computer readable medium storing executable instructions that, when executed by a processor, cause the processor to:
receive first samples for a first time window of a signal;
receive second samples for a second time window of the signal, the second time window after the first time window;
determine a first frequency domain spectrum using the first samples;
determine a second frequency domain spectrum using the second samples;
determine first pulse rates for the first time window based on the first frequency domain spectrum;
determine second pulse rates for the second time window based on the second frequency domain spectrum;
determine a third pulse rate based on the first pulse rates and the second pulse rates.

14. The non-transitory computer readable medium of claim 13, further storing instructions, when executed by the processor, cause the processor to:
determine differences between the first pulse rates and the second pulse rates;
determine transition pairs by pairing each one of the first pulse rates with a respective one of the second pulse rates;
determine a metric of each transition pair based on a difference between the one of the first pulse rates and the one of the second pulse rates of the transition pair;
rank at least some of the transition pairs based on the metrics; and
select one of the second pulse rates of one of the transition pairs as the third pulse rate based on a result of the ranking.

15. The non-transitory computer readable medium of claim 14, wherein the metric includes at least one of: a first component that decreases as the differences increase.

16. The non-transitory computer readable medium of claim 14, wherein the metric includes a component that reflects an activity state of an object, and the third pulse rate is of the object.

17. The non-transitory computer readable medium of claim 14, wherein the differences are first differences, and the metric includes a component that reflects a second difference between the one of the first pulse rates of the one of the transition pairs and a fourth pulse rate in a third time window prior to the first time window.

18. The non-transitory computer readable medium of claim 14, further storing instructions that, when executed by the processor, cause the processor to:
exclude a first transition pair of the transition pairs from the ranking based on the difference between one of the first pulse rates and one of the second pulse rates of the first transition pair exceeding a threshold.

19. The non-transitory computer readable medium of claim 14, further storing that, when executed by the processor, cause the processor to:
exclude a first transition pair of the transition pairs from the ranking based on the metric of the first transition pair being below a threshold.

20. The non-transitory computer readable medium of claim 19, wherein the threshold is based on a maximum metric among the metrics of the transition pairs.

21. The non-transitory computer readable medium of claim 13, further storing instructions that, when executed by the processor, cause the processor to:
filter the first samples and the second samples to generate, respectively, filtered first samples and filtered second samples;
perform motion compensation processing on the filtered first samples and the filtered second samples to generate, respectively, first motion compensated values and second motion compensated values;
determine the first frequency domain spectrum based on performing a first Fourier transform operation on the first motion compensated values; and determine the second frequency domain spectrum based on performing a second Fourier transform operation on the second motion compensated values.

22. The non-transitory computer readable medium of claim 13, further storing instructions that, when executed by the processor, cause the processor to:

identify first frequency components from the first frequency domain spectrum based on a prior pulse rate for a prior time window;

determine the first pulse rates based on the first frequency components;

identify second frequency components from the second frequency domain spectrum based on the prior pulse rate; and determine the second pulse rates based on the second frequency components.

23. An apparatus comprising:
an analog to digital converter (ADC); and
a processor circuit configured to:
  receive, from the ADC, first samples for a first time window of a signal;
  receive, from the ADC, second samples for a second time window of the signal, the second time window after the first time window;
  determine a first frequency domain spectrum using the first samples;
  determine a second frequency domain spectrum using the second samples;
  determine first pulse rates for the first time window based on the first frequency domain spectrum;
  determine second pulse rates for the second time window based on the second frequency domain spectrum; and
  determine a third pulse rate based on the first pulse rates and the second pulse rates.

* * * * *